United States Patent
Stocco (10) Patent No.: US 11,690,897 B2
(45) Date of Patent: Jul. 4, 2023

(54) SALT INDUCIBLE KINASE INHIBITORS FOR ENHANCING FERTILITY

(71) Applicant: The Board of Trustees of the University of Illinois, Urbana, IL (US)

(72) Inventor: Carlos Stocco, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 16/781,307

(22) Filed: Feb. 4, 2020

(65) Prior Publication Data

US 2020/0246435 A1    Aug. 6, 2020

Related U.S. Application Data

(60) Provisional application No. 62/800,722, filed on Feb. 4, 2019.

(51) Int. Cl.
*A61K 38/24* (2006.01)
*A61P 15/08* (2006.01)
*A61K 31/138* (2006.01)

(52) U.S. Cl.
CPC ............ *A61K 38/24* (2013.01); *A61K 31/138* (2013.01); *A61P 15/08* (2018.01)

(58) Field of Classification Search
None
See application file for complete search history.

(56) References Cited

U.S. PATENT DOCUMENTS

| | | | |
|---|---|---|---|
| 9,586,975 | B2 | 3/2017 | Blom |
| 9,670,165 | B2 | 6/2017 | Cohen |
| 9,890,153 | B2 | 2/2018 | Vankayalapati |
| 10,265,321 | B2 | 4/2019 | Shamji |

FOREIGN PATENT DOCUMENTS

| | | |
|---|---|---|
| WO | 2013136070 A1 | 9/2013 |
| WO | 2014093383 A1 | 6/2014 |
| WO | 2018053373 A1 | 3/2018 |

OTHER PUBLICATIONS

Armouti et al., Endocrinology, Jul. 2020, 161(7):1-13 (Year: 2020).*
Sundberg et al., ACS Chem. Biol. 2016, 11,2105-2111 (Year: 2016).*
Wein et al., Trends in Endocrinology & Metabolism, Oct. 2018, vol. 29, No. 10 (Year: 2018).*
Pirollo et al., Cancer Res. 2008; 68(5): 1247-1250 (Year: 2008).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Rong et al. 2019, J. Thorac. Oncol. 14: 1766-1783 (Year: 2019).*
Yao et al., Cancer Biology & Therapy, 2006; 5: 1179-1186 (Year: 2006).*
Hu et al., Signal Transd. Target. Ther. 5:101 (Year: 2020).*
Lindheim et al., The Journal of Obstetrics and Gynecology of India (Jul.-Aug. 2018) 68(4): 242-252 (Year: 2018).*
Tatiparti et al., Nanomaterials 2017, 7, 77; doi:10.3390/nano7040077 (Year: 2017).*
Gilchrist and Ritter, Reproduction (2011) 142 647-657 (Year: 2011).*
Bowdridge et al., Reproductive Biology and Endocrinology (2017) 15:76 (Year: 2017).*
Ozanne, J., A.R. Prescott & K. Clark (2015) "The clinically approved drugs dasatinib and bosutinib induce anti-inflammatory macrophages by inhibiting the salt-inducible kinases," Biochem. J. 465(Pt 2):271-9.
Sundberg, T.B., H.G. Choi, J.-H. Song, C.N. Russell, M.M. Hussain, D.B. Graham, B. Khor, J. Gagnon, D.J. O'Connell, K. Narayan, V. Dancik, J.R. Perez, H.-C Reinecker, N.S. Gray, S.L. Schreiber, R.J. Xavier, & A.F. Shamji (2014) "Small-molecule screening identifies inhibition of salt-inducible kinases as a therapeutic strategy to enhance immunoregulatory functions of dendritic cells," Proc. Natl. Acad. Sci. USA 111(34):12468-73.

* cited by examiner

*Primary Examiner* — Christina M Borgeest
(74) *Attorney, Agent, or Firm* — Licata & Tyrrell P.C.

(57) ABSTRACT

This invention relates to methods of using salt inducible kinase inhibitors to enhance female fertility.

32 Claims, 6 Drawing Sheets

SALT INDUCIBLE KINASE INHIBITORS FOR ENHANCING FERTILITY

INTRODUCTION

This application claims benefit of priority to U.S. Provisional Patent Application Ser. No. 62/800,722, filed Feb. 4, 2019, the content of which is incorporated herein by reference in its entirety.

This invention was made with government support under grant nos. HD086054 and HD097202, awarded by the National Institutes of Health. The government has certain rights in this invention.

BACKGROUND

Infertility affects approximately 15% of human couples. Moreover, women over the age of 35, who have postponed maternity face the natural limits of their reproductive system. A frequent and increasing problem restricting fertility is anovulation. Thus, the population of women undergoing ovulation induction and controlled ovarian stimulation has expanded worldwide. Therefore, controlling negative regulators of ovulation could reduce the burden of infertility.

The somatic cells of the ovarian follicle, namely the granulosa cells, play a vital role in the coordination of folliculogenesis by integrating oocyte, theca cells, and pituitary signals. Granulosa cell differentiation from the preantral into the preovulatory stage of follicular development and later via luteinization into luteal cells is essential for the coordination of ovulation, fertilization, and uterine receptivity. As nurse cells, cumulus granulosa cells are necessary for oocyte development and survival. As endocrine cells, mural granulosa cells produce high amounts of estradiol, particularly toward the middle of the ovarian cycle, contributing to coordinate ovulation, the pinnacle of folliculogenesis. Estradiol production and antral follicle growth depend on follicle-stimulating hormone (FSH). Consequently, FSH is the primary hormone used to stimulate follicle growth in women undergoing assisted reproductive technology, although the response of patients to FSH can vary widely, ranging from a poor to strong response. Inadequate response to FSH results in fewer retrieved eggs, leading to lower pregnancy rates. Currently, the most common clinical approach to improving pregnancy rates is to use higher doses of FSH, even though this approach does not have a clear advantage and could lead to ovarian hyperstimulation. Thus, there is a need in the art to identify limiting factors that, when inhibited, could enhance the response of granulosa cells to FSH.

In females, FSH targets exclusively ovarian granulosa cells. FSH activates receptor-associated Ga proteins, which stimulate adenylate cyclase activity and the production of cyclic AMP (cAMP). The control of gene expression in response to cAMP is mediated by salt-inducible kinases (SIKs). The three SIK isoforms (SIK1, SIK2, and SIK3) are serine/threonine kinases known to regulate metabolism, cancer, melanocytes, and bone formation (Hardie & Carling (1997) *Eur. J. Biochem.* 246(2):259-273; Wein, et al. (2018) *Trends Endocrinol. Metabol.* 29(10):723-35) and have been implicated in sensitivity of cancer cells to conventional chemotherapeutics (Zhou, et al. (2017) *Clin. Cancer Res.* 23(8):1945-54; WO 2018/193084 A1). In addition, SIK inhibitors have been described for use in the treatment of inflammation, e.g., inflammatory bowel disease or graft-versus-host disease (US 2017/0224700 A1; WO 2013/136070 A1) osteoporosis (WO 2018/053373 A1), metabolic disorders (WO 2006/034007 A2), cancer, stroke, obesity, diabetes and cardiovascular disease (U.S. Pat. No. 9,890,153 B2). However, a role for SIKs in modulating folliculogenesis has not been described.

SUMMARY OF THE INVENTION

This invention provides methods for improving, restoring or enhancing fertility and for increasing oocyte production in a female subject by administering to the female subject an effective amount of an inhibitor of salt-inducible kinase 2 (SIK2). In some embodiments, the inhibitor of SIK2 is used in combination with an agent of an ovulation induction regimen, e.g., a gonadotropin-releasing hormone agonist, human menopausal gonadotropin, follicle-stimulating hormone, clomiphene citrate or human chorionic gonadotropin. In other embodiments, the female subject has a diminished ovarian response to gonadotropins or is older than 35 years of age. A kit including an inhibitor of SIK2 and one or more agents of an ovulation induction regimen is also provided.

BRIEF DESCRIPTION OF THE DRAWINGS

FIG. 1A-1B show that SIK inhibition potentiates FSH actions in rat granulosa cells. Rat granulosa cells were treated with vehicle, FSH, FSH plus HG-9-91-01 (HG; FIG. 1A), FSH plus MRT67307 (MRT; FIG. 1B), or SIK inhibitors alone. Cyp19a1 mRNA levels were quantified 48 hours later and expressed as relative levels to ribosomal L19 protein (Rp119).

FIG. 3A-3F show that SIK inhibition enhances FSH actions in primary human granulosa cells. FIG. 3A and FIG. 3B respectively show aromatase mRNA and promoter activity in primary human granulosa cells after treatment with vehicle, FSH, FSH+HG-9-91-01 (HG), or HG alone for 48 hours.

FIG. 5A-5D show that SIK2 knockdown mimics the pharmacological inhibition of SIK activity. FIG. 5A, Expression of each SIK isoform in rat granulosa cells exposed to scrambled oligos (shSCR) or anti-SIK1 (shSIK1), SIK2 (shSIK2), or SIK3 (shSIK3) shRNAs. *$p<0.05$, $p<0.01$, t-test, n=3.

FIG. 8A-8B show that SIK inhibition enhances FSH actions in vivo. FIG. 8A, Primary rat granulosa cells were treated with vehicle, FSH, FSH plus YKL-05-099 (YKL), or YKL alone. Cyp19a1 mRNA levels were quantified 48 hours later and expressed as relative levels to Rp119. Different letters represent significant differences (mean±SEM, n=5, one-way ANOVA followed by Tukey, $p<0.05$).

DETAILED DESCRIPTION OF THE INVENTION

Follicle development is the most crucial step toward female fertility and relies mainly on the actions of FSH. Consequently, FSH is the primary hormone used to stimulate follicle development in patients with ovulatory dysfunctions. However, FSH is not always effective. In particular, a certain percentage of women undergoing infertility treatments respond poorly to FSH stimulation and have lower pregnancy rates compared with normal responders due to poor follicle production leading to a smaller number of eggs. Poor ovarian response is the first sign of ovarian aging (early ovarian failure or early menopause). Thus, woman in her forties or that have low ovarian reserve do not produce an optimal number of oocytes during IVF procedures. Moreover, even young woman that have apparently normal ovarian reserve may also unexpectedly respond poorly to IVF procedures.

It has now been found that salt-inducible kinase 2 (SIK2) opposes FSH actions. Characterization studies show that all SIK isoforms are present in human and rodent granulosa cells. The knockdown of each SIK isoform separately demonstrates that SIK2 plays a significant role in controlling FSH actions. In humans, SIK inhibition strongly enhances FSH stimulation of aromatase in patients with normal ovarian function and recovers FSH action is patients with the polycystic ovarian syndrome. Administration of SIK inhibitors to female mice before the administration of PMSG, a hormone with FSH activity, enhances granulosa cell differentiation. These findings demonstrate the involvement of SIK2 in the regulation of granulosa cell differentiation in humans and mice. Thus, pharmacological modulation of SIK2 activity finds use in treating ovulatory defects in humans, reducing the dose of gonadotropins used in normal responder patients, preserving endangered mammals, and increasing reproductive yield in livestock.

Accordingly, this invention is directed to compositions and methods for improving, restoring, recovering or enhancing fertility by inhibiting the activity of SIK2. In particular, a SIK2 inhibitor is used in the methods of this invention to improve ovarian function in female subjects, e.g., subjects with diminished ovarian response to controlled ovarian stimulation; enhance, restore or improve fertility in a female subject; enhance, restore or improve the response of a female subject to gonadotropins; enhance or improve ovarian response in a poor ovarian response (POR) female subject; enhance, restore or improve ovarian response in a human female subject older than about 35 years; increase oocyte production or release in a female subject; and/or enhance or increase ovarian response to follicle stimulating treatments.

As is known in the art, "salt-inducible kinase 2," "SIK2" or "serine/threonine-protein kinase SIK2" in humans is a 120 kD protein, the amino acid sequence of which is known and available under GENBANK Accession No. NP_056006.1. Orthologs of the human SIK2 protein have bene identified in 297 organisms. SIK2 belongs to an AMP-activated protein kinase family and is required for bipolar mitotic spindle formation. The terms "SIK2 inhibitor" and "inhibitor of SIK2" are used interchangeably and refer to compounds that reduce, slow, halt, and/or prevent expression (e.g., the amount), function, activity and/or stability of SIK2, especially of mRNA encoding SIK2 and/or SIK2 protein in a cell relative to a control, e.g., a vehicle control.

A SIK2 inhibitor may impair, suppress, reduce and/or lower the expression of SIK2 (e.g., SIK2 mRNA or protein) in a cell. The term "expression" means in this context the cellular process of transcribing a gene into an mRNA and the following translation of the mRNA into a protein. "Gene expression" therefore may thus refer to the generation of mRNA and/or translation of the expressed mRNA into a protein. The term "protein expression" on the other hand may refer to the complete cellular process of synthesis of proteins and/or transport/localization thereof into certain cellular compartments. A SIK2 inhibitor may impair (e.g., induce a decrease or reduction in) the efficiency, effectiveness, amount or rate of one or more activities of SIK2 (for example, by impairing the expression of SIK2 protein), such as one or more of those activities described herein. A SIK2 inhibitor may have a negative effect toward the stability of SIK2 (e.g., SIK2 mRNA or protein), which shall be understood in its broadest sense, and shall include inhibitors which, for example, interfere with and reduce the SIK2 protein half-life or interfere with and disturb SIK2 protein folding, protein presentation or transport/localization within the cell.

A SIK2 inhibitor can act directly, for example, by binding to SIK2 and decreasing the amount or rate of one or more of the properties of SIK2 such as its expression, function and/or stability, in particular its ability to act as a kinase, for example by reducing the amount or activity of SIK2 in the cell. A SIK2 inhibitor may, alternatively, act indirectly, for example, by binding to a regulatory molecule or gene region to modulate such regulatory protein or gene region function and hence consequentially affect a decrease in the amount or rate of SIK2 expression (e.g., amount), function/activity and/or stability, in particular by impairing one or more activity of SIK2 protein or mRNA (such as by changing the amount or rate of expression and/or stability of SIK2 protein or mRNA). Preferably, the SIK2 inhibitor acts directly on SIK2. Non-limiting examples of SIK2 inhibitors that act directly on SIK2 include: (i) siRNA or shRNA molecules that bind to and reduce expression of SIK2 mRNA; (ii) small molecule moieties that bind to SIK2 and reduce the activity of SIK2; or (iii) antagonistic SIK2 antibodies.

When a compound, pharmaceutical composition, kit, method, or use is referred to as "selectively" or "specifically" inhibiting the activity of a first protein kinase, the compound, pharmaceutical composition, kit, method, or use modulates the activity of the first protein kinase to a greater extent (e.g., not less than about 2-fold, not less than about 5-fold, not less than about 10-fold, not less than about 30-fold, not less than about 100-fold, not less than about 1000-fold, or not less than about 10000-fold) than the activity of at least a second protein kinase that is different from the first protein kinase. In accordance with some aspects of the invention, SIK2 is selectively inhibited by the compound, pharmaceutical composition, kit, method or use described herein, compared to SIK1, SIK3, or a protein kinase that is not a SIK.

SIK2 inhibitors of use in this invention include those known in the art as well as those identified in a screening assay for SIK2 inhibitors. Examples of SIK2 inhibitors known in the art include, but are not limited to, compounds having the structures listed in Table 1, and pharmaceutically acceptable salts thereof.

TABLE 1

| SIK2 Inhibitors | Source |
|---|---|
| <br>1H-pyrrolo[2,3-b]pyridine and 1H-pyrazolo[3,4-b]pyridine derivatives | U.S. Pat. No. 9,890,153 |
| <br>Macrocyclic pyrazolopyrimidines and imidazopyridazines derivatives | U.S. Pat. No. 9,586,975 |
|  | U.S. Pat. No. 10,265,321 |

TABLE 1-continued

| SIK2 Inhibitors | Source |
|---|---|

Macrocyclic, imidazoyl, urea and carbamate derivatives

WO 2018053373

U.S. Pat. No. 9,670,165

2,4-diaminopyrimidine derivatives

US Patents cited above are incorporated by reference in their entireties.

Exemplary SIK2 inhibitors useful in this invention, include, but are not limited, compounds having the structures listed in Table 2, and pharmaceutically acceptable salts thereof.

TABLE 2

| SIK2 Inhibitors | SIK2 $IC_{50}$ |
|---|---|
| HG-9-91-01 (CAS No. 1456858-58-4) | 6.6 nM |
| MRT67307 (CAS No. 1190379-70-4) | 250 nM |
| MRT199665 (CAS No. 1456858-57-3) | 12 nM |
| Dorsomorphin (Compound C; CAS No. 866405-64-3) | NA |
| YKL-05-099 (CAS No. 1936529-65-5) | 40 nM |
| YKL-06-061 (CAS No. 2172617-15-9) | 1.77 nM |
| KIN-112 (WH-4-023; CAS No. 837422-57-8) | NA |
| ARN3236 (CAS No. 1613710-01-2) | <1 nM |
| Dasatinib (CAS No. 302962-49-8) | <3 nM |
| Bosutinib (CAS No. 380843-75-4) | <3 nM |
| TAE-684 (CAS No. 761439-42-3) | NA |

NA, not available.

The above-referenced SIK2 inhibitors are described in the art and/or available from commercial sources such as MedChemExpress, Monmouth Junction, N.J.; Tocris Bioscience, Bristol, UK; or AbCam, Cambridge, UK. See also U.S. Pat. No. 9,890,153, which discloses ARN3236 and its analog ARN3261; WO 2013/136070, WO 2014/093383; Ozanne, et al. (2015) *Biochem. J.* 465(Pt 2):271-9; Sundberg, et al. (2014) *Proc. Natl. Acad. Sci. USA* 111(34):12468-73).

In some aspects, the SIK2 inhibitor is in the form of a pharmaceutically acceptable salt. As used herein, the term "pharmaceutically acceptable salt" refers to those salts of SIK2 inhibitors which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well-known in the art. See, e.g., Berge, et al. (1977) *J. Pharmaceutical Sciences* 66:1-19. Salts can be prepared in situ during the final isolation and purification of a SIK2 inhibitor, or separately by reacting a free base with a suitable organic acid. Examples of pharmaceutically acceptable salts include, but are not limited to, nontoxic acid addition salts formed from amino group and an inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

This invention provides methods for improving, restoring or enhancing fertility and increasing oocyte production in a female subject by administering an effective amount of a SIK2 inhibitor. As used herein, "fertility" refers to the ability to produce offspring. "Enhancing fertility" mean enhancing ovulatory function in a female treated with a SIK2 inhibitor of the invention relative to ovulatory function in the female subject in the absence of treatment. Enhanced ovulatory function may be measured, for example, as in increase in the number of oocytes produced by the female subject in the presence and absence of treatment. "Restoring fertility" means rescuing or recovering ovulatory function in a female treated with a SIK2 inhibitor of the invention relative to ovulatory function in the female subject in the absence of treatment. Restoring fertility is of particular use in a female subject with abnormal ovarian function, a female subject with diminished ovarian response to gonadotropins, or in an older female exhibiting a decline in fertility.

Accordingly, for the purposes of this invention, a subject female to be treated with a SIK inhibitor may have normal ovarian function or abnormal ovarian function (e.g., polycystic ovarian syndrome or anovulation), and is in need of an increase in the number of oocytes released, a restoration or improvement in response to gonadotropins, or an enhancement in the time to achieve pregnancy. The female subject can be any mammal, including, but not limited to, humans, mice, rats, rabbits, dogs, cats, guinea pigs, hamsters, cows, horses, pigs, sheep, goats, etc. In particular embodiments, the subject female to be treated with a SIK inhibitor is a human female subject older than 35 years of age.

Preferably, the methods of the invention are carried out during the follicular phase of the mammal. "Follicular phase" refers to the first part of the menstrual cycle and is characterized by a progressive increase in circulating levels of estradiol and inhibin B by the developing Graafian follicle.

In certain aspects, a SIK2 inhibitor may be used to improve the quality and/or quantity of oocytes that ultimately can be fertilized in situ. In other aspects, a SIK2 inhibitor may be used to improve the quality and/or number of oocytes appropriate for retrieval for an in vitro fertilization or harvest procedure. In some embodiments, the female subject helped by the compounds, compositions and methods of this invention may require or be positively affected by improved fertility or improved fertility potential in situ or via an in vitro protocol, or a process for preparation for a fertility promoting procedure in situ or in vitro. Accordingly, in some embodiments, the subject is participating in a natural conception or an assisted reproduction technology (ART) such as artificial insemination, in vitro fertilization (IVF), gamete intrafallopian transfer (GIFT), intra-uterine insemination (IUI), or intracytoplasmic sperm injection (ICSI) protocol.

As used herein, the term "effective amount" or "pharmaceutically effective amount" refers to a nontoxic but sufficient amount of a compound, composition, formulation and/or dosage form as described herein that may be effective to achieve a particular biological result. Such results may include, but are not limited to, enhancement in the reproductive capability, fertility, response to gonadotropin, oocyte production or release, aromatase expression, and/or estradiol production. An effective amount of a SIK2 inhibitor to improve, restore or enhance fertility or increase oocyte production refers to an amount that causes an animal to demonstrate greater fertility or oocyte production than an animal would otherwise demonstrate in the absence of the SIK2 inhibitor under otherwise prevailing conditions. An appropriate "effective" amount in any individual case can be determined by one of ordinary skill in the art using routine experimentation.

In some aspects, the SIK inhibitor is used in combination with an ovulation induction regimen. An "ovulation induction regimen" refers to a current method of promoting folliculogenesis and induced ovulation. Such ovulation induction regiments include one or a combination of the agents listed in Table 3.

TABLE 3

| Agent | Tradename | Function |
| --- | --- | --- |
| Gonadotropin-Releasing Hormone (GnRH) agonists (leuprolide acetate or nafarelin acetate) | LUPRON ® or SYNAREL ® | Suppress ovaries during IVF, GIFT, or other ART retrieval cycles to prevent premature ovulation prior to egg retrieval. |
| Human Menopausal Gonadotropin (hMG) | PERGONAL ®, HUMEGON ® or REPRONEX ® | Contain FSH and LH, typically used to stimulate ovaries during ART procedures or for women who do not respond to Clomiphene therapy. |
| Follicle Stimulating Hormone (FSH) | FOLLISTIM ®, GONAL-F ®, BRAVELLE ® or FERTINEX ® | Often prescribed for patients who fail to respond to clomiphene or for ART procedures. |
| Clomiphene Citrate | CLOMID ® or SEROPHENE ® | Stimulates ovulation for women with irregular menstrual cycles or to stimulate the development of extra eggs. |
| Human Chorionic Gonadotropin (hCG) | PROFASI ®, PREGNYL ®, or OVIDREL ® | Often used to simulate LH surge in ART cycles to induce exactly timed ovulation. |

Ovulation induction regimens are varied in terms of the timing, frequency and concentration of the agents administered. Certain principles do apply, however, and provide the basis for safe and effective treatment. However, it should be noted that the criteria set forth below for inducing ovulation is given for example purposes only and may vary significantly by clinic, patient and the goal of the treatment.

The first cycle usually involves the administration of FSH daily beginning on day 4 to 7 of a withdrawal bleed. Follicle growth and response are monitored by both estrogen levels and ultrasound. Adequate follicle stimulation is usually achieved by 7 to 14 days of continuous FSH administration. Accordingly, in a particular embodiment, the ovulation induction regimen includes the use of FSH.

Once sufficient follicle development has been achieved (two 16- to 18-mm follicles together with a progressive rise in serum estrogen to 500 to 1,000 pg/mL), hCG (5,000 or 10,000 IU) is administered. Following administration of hCG, the couple is instructed to have intercourse on that night and once or twice more over the next 48 hours.

The fundamental rule regarding gonadotropin administration is that each and every treatment cycle must be individualized, monitored, and adjusted appropriately. Monitoring is necessary not only to enhance ovulation and pregnancy rates but also to reduce the risk of severe ovarian hyperstimulation and its potential consequences and multiple pregnancies. This is achieved by frequent determinations of plasma/serum estradiol levels and by inspection of the ovaries by ultrasound. Estradiol levels generally correlate with the number of growing follicles but not necessarily with the number of mature follicles. Because follicular growth correlates directly with ovum maturation, ultrasound assessment of mean follicular diameter may be used as an indicator in assessing maturity and timing of hCG administration.

The goal of most treatments is to maximize the potential for a singleton pregnancy while reducing the risk of hyperstimulation syndrome. Estradiol levels between 1000 and 1500 pg/mL appear to be optimal, but actual levels may vary depending on the laboratory used and the physician's experience. The risk of hyperstimulation increases with higher estradiol levels. In general, when serum estradiol exceeds 2000 pg/mL, hCG should be administered with great caution or withheld to allow follicles to regress.

In various embodiments, the SIK2 inhibitor may be administered before, after, or simultaneously with an agent of the ovulation induction regimen.

Ideally, the SIK2 inhibitor is administered in the form of a pharmaceutical composition including an effective amount of a SIK2 inhibitor as described herein, and one or more pharmaceutically acceptable diluents, preservatives, solubilizers, emulsifiers, adjuvants, excipients, or carriers. In some aspects, the SIK2 inhibitor is administered in the form of a pharmaceutical composition including an effective amount of a SIK2 inhibitor as described herein, and one or more pharmaceutically acceptable excipients or vehicles, and optionally one or more other therapeutic and/or prophylactic ingredients.

"Pharmaceutically acceptable" vehicles, diluents, adjuvants, excipients or carriers are well known in the pharmaceutical art, and are described, for example, in Remington's Pharmaceutical Sciences, 18th Edition (Easton, Pa.: Mack Publishing Company, 1990). By way of illustration, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, a pharmaceutical composition can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

In general, the compositions of the disclosure will be administered in an effective amount by any of the accepted modes of administration. Suitable dosage ranges depend upon numerous factors such as the severity of the disease to be treated, the age and relative health of the subject, the potency of the compound used, the route and form of administration, the indication toward which the administration is directed, and the preferences and experience of the medical practitioner involved. One of ordinary skill in the art will be able, without undue experimentation and in reliance upon personal knowledge and the disclosure of this application, to ascertain an effective amount of the compositions of the disclosure.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction. For example, doses of the orally bioavailable SIK2 inhibitor ARN3261 in mice have ranged from 20-100 mg/kg (about 1.6-8 mg/kg in humans) and been shown to effectively inhibit ovarian tumor growth without toxicity.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria-retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be achieved using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

In accordance with the method of the invention, an effective amount of the composition will be delivered to the subject to improve, restore or enhance fertility or increase oocyte production in the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the disclosure, generally an effective amount may be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to achieve the desired outcome.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In some aspects, the invention provides a kit for use in the methods described herein. A kit of invention includes a SIK2 inhibitor and one or more agents of an ovulation induction regimen. In addition, the kit may optionally include instructions for its use. In some embodiments, the kit includes sufficient daily doses of FSH and/or a compound having FSH effect, preferably clomiphene to cause follicular maturation, and an effective dose of a SIK2 inhibitor, and instructions for the use of the kit in ovulation induction or ART.

The following non-limiting examples are provided to further illustrate the present invention.

Example 1: Materials and Methods

Human Granulosa Cells. Human cells were collected from the follicular aspirates of women undergoing in vitro fertilization treatment at the University of Illinois at Chicago Fertility Center, under Institute Review Board approval. Informed consents were obtained from all women. In a subset of patients, additional information was collected to compare the effect of SIK inhibition in patients with different etiologies. Cells were transported immediately to the laboratory where they were dispersed by hyaluronidase digestion (8 IU/µl) and then centrifuged at 500×g for 5 minutes. Cells were incubated at room temperature in red blood cell lysis buffer for 2 minutes to eliminate contaminating erythrocytes. The cells were again centrifuged at 500×g for 5 minutes and suspended in 0.5 ml of serum-free DMEM/F12-0.25% BSA medium containing antibiotics. To investigate mRNA expression, cells were plated at a density of 30000 cells/well in 24-well plates coated with reconstituted basement membrane sold under the tradename Matrigel® (DB Biosciences). To investigate protein expression, cells were plated at a density of 200000 cells/well in 6-well plates coated with reconstituted basement membrane sold under the tradename Matrigel® (DB Biosciences). Cells were treated with human recombinant FSH (Serono) with or without specific inhibitors of SIKs: HG-9-91-01 (HG), MRT67307 (MRT), or compound C (CoC), all obtained from Tocris (Bristol, United Kingdom) or MedChemExpress (Monmouth Junction, N.J.). Each data point reflects a result obtained from individual patients. Cells from each patient were cultured separately.

Rat Granulosa Cells. Rat granulosa cells were isolated from immature rats treated with estradiol for three days. Cells were cultured and treated as described for human granulosa cells. Rat experiments were approved by the Biologic Resources Laboratory (BRL) of the University of Illinois at Chicago.

In vivo Treatment with SIK Inhibitors. Immature mice between 21 and 23 days old were intraperitoneally injected with YKL-05-099 (MedChemExpress, 10 mg/kg) suspended in phosphate-buffered saline (PBS). Two hours later, mice were injected again with the same dose of YKL-05-099 along with 4 IU pregnant mare serum gonadotropin (PMSG; Sigma, San Louis, Mo.). Controls were injected with 4 IU PMSG alone. granulosa cells were collected 48 hours after PMSG.

mRNA Quantification. Total RNA was isolated at the end of each experiment using TRIzol™ reagent (Invitrogen) according to the manufacturer's protocol. The isolated RNA was reverse-transcribed using anchored oligo-dT primers (IDT, Coralville, Iowa) and Moloney Murine Leukemia Virus reverse transcriptase (Invitrogen) at 37° C. for 1 hour. The resulting cDNA was diluted with water to a final volume of 100 µl and 5 µl of diluted cDNA was used for each qPCR reaction. Gene expression is reported relative to ribosomal protein L19 mRNA (Rp119).

Immunoblot Analysis. Cells were harvested in ice-cold RIPA lysis buffer supplemented with protease inhibitors (Sigma). Protein concentration and Western blot analysis of cell lysates were performed as previously described (Bennet, et al. (2013) *Endocrinology* 154(12):4845-58). Antibodies against Aromatase (1:1000; Abcam), ACTB (RRID: AB_303668; 1:1000; Proteintech) and CYP19a1 (RRID: AB_10703956) were used to detect protein expression by western blot as previously described (Baumgarten et al. (2014) *J. Clin. Endocrinol. Metab.* 99(8):2995-3004).

Estradiol Measurement. Cell culture medium used for steroid determinations by ELISA (DRG Instruments; RRID: AB_2756386)) following manufacturer's instructions.

Immunohistochemistry and Fluorescent Studies. Ovaries were fixed in Bouin's Solution prior to paraffin embedding. Five µM sections were dewaxed and rehydrated. This was followed by antigen retrieval using citrate buffer solution (10 mM of citric acid and sodium citrate, pH 6) microwaved on high for 30 seconds until boiling and then at low for 8 more minutes. After cooling, slides were placed in 1% $H_2O_2$. Sections were then blocked using a Avidin/Biotin Blocking kit (Vector Laboratories, Burlingame, Calif.) followed by 30 minutes of blocking in superblock blocking buffer (Pierce Chemicals, Rockford, Ill.) prior to the addition of the primary antibody diluted in PBS (SIK1, 1:200, RRID: AB_2301724; SIK2, 1:200, RRID: AB_11140583; SIK3, 1:200, RRID: AB_2042747). Following washes with T-PBS, slides were incubated in secondary antibody for 30 minutes at room temperature followed by washing. Tissues were stained via the 3,3-diaminobenzidine chromogen and ABC kit sold under the tradename VECTASTAIN® ELITE® ABC (Vector laboratories) following the manufacturer's recommendations. Slides were counterstained with Gill's hematoxylin prior to mounting.

The same antibodies used in immunostaining were also used for immunofluorescence staining of cultured granulosa cells, with the exception that visualization was performed using Cy3-conjugated streptavidin (diluted 1:6000 in PBS; Jackson, West Grove, Pa.). Ovarian sections were also stained with Hematoxylin and counterstained with Eosin.

Statistics. Data were analyzed using Prism 6 (San Diego, Calif.). Differences between two groups were determined by Student's t-test. For multiple groups, one-way ANOVA was used and differences between individual means were determined by the Tukey test. Data are represented as mean±SEM. Significant difference was recognized at $P<0.05$.

Figure 1A:
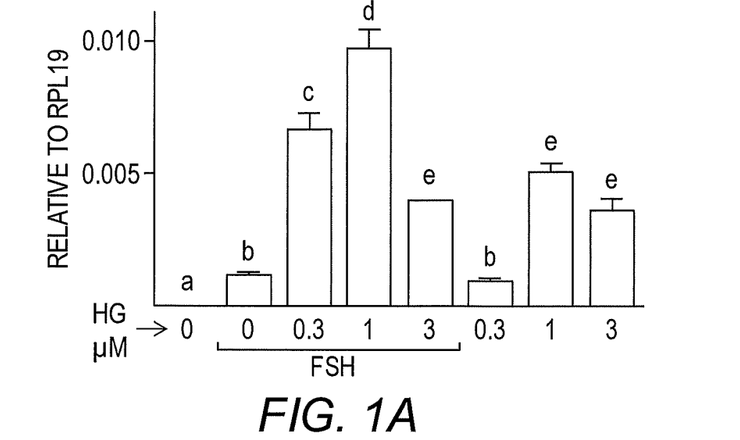
Figure 1B:
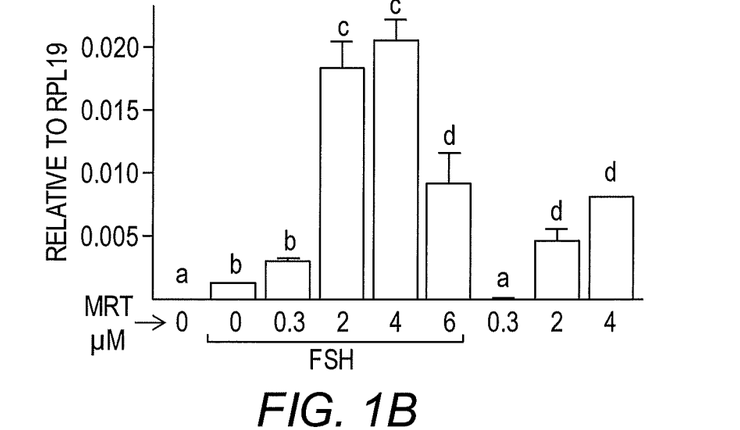

Example 2: Pharmacological Inhibition of SIK Activity Enhances FSH Actions in Rodents To demonstrate that SIK activity plays a role in the regulation of granulosa cell function, SIK activity was ablated using HG-9-91-01 (HG), a SIK inhibitor whose potency and specificity have been well-characterized (Patel, et al. (2014) *Nat. Communic.* 5:4535). FSH actions center on the stimulation of the CYP19a1 gene, which encodes for the estrogen-producing enzyme aromatase (Stocco (2012) *Steroids* 77(1-2):27-35). Therefore, CYP19a1 expression and activity were used to evaluate the effects of SIK inhibition. In rat and mouse granulosa cells, SIK inhibition potentiated FSH-stimulation of aromatase in a concentration-dependent manner (FIG. 1A); however, a stronger potentiation was observed with the lower concentrations (0.3 and 1 µM) than with the higher concentration (3 µM) of the inhibitor used. In the absence of FSH, treatment with 1 or 3 µM of the SIK inhibitor increased Cyp19a1 mRNA levels. Comparable findings were seen using SIK inhibitor MRT67307 (FIG. 1B).

To determine whether the effect of SIK inhibition on Cyp19a1 mRNA levels was mediated by an increase in the expression of the Cyp19a1 gene, granulosa cells were infected with a reporter controlled by the CYP19a1 proximal promoter. Luciferase activity was detectable but low in the absence of FSH while FSH stimulated reporter activity by 20-fold. Co-treatment with the SIK inhibitor enhanced the stimulatory effect of FSH on aromatase promoter activity in a concentration-dependent manner. No activity was observed in cells infected with an empty reporter. Treatment with the SIK inhibitor alone increased Cyp19a1 promoter activity.

Figure 2:
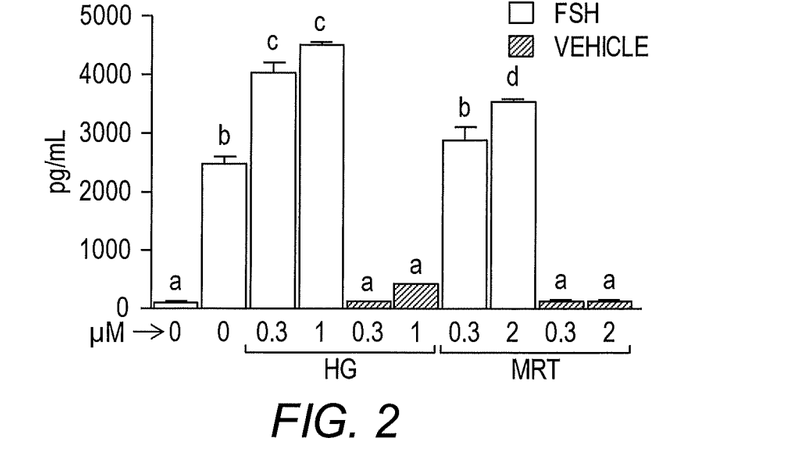
FIG. 2 shows that estradiol production is potentiated by SIK inhibition. Mouse granulosa cells were treated with FSH or vehicle plus SIK inhibitors HG-9-91-01 (HG) or MRT67307 (MRT) for 48 hours. Estradiol was determined by ELISA. Different letters differ significantly, (n=5).

Aromatase drives the production of estradiol, a steroid hormone playing a central role in the regulation of all aspects of female reproductive activity. Consequently, the effect of SIK inhibition on estradiol production by granulosa cells was examined. Inhibition of SIK activity using either HG-9-91-01 or MRT67307 potentiated the stimulation of estradiol production by FSH in a dose-dependent manner (FIG. 2).

Figure 3A:
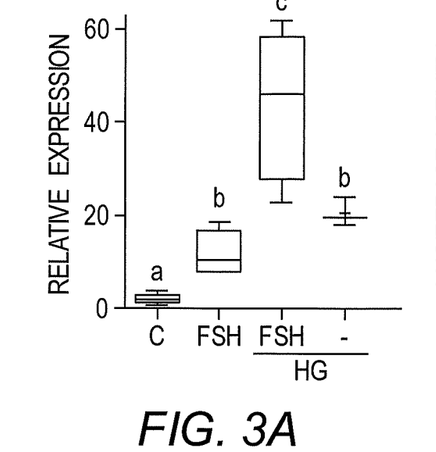
Figure 3B:
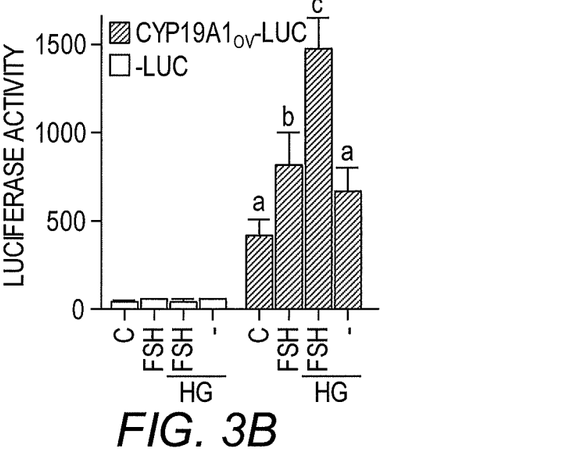
Figure 3C:
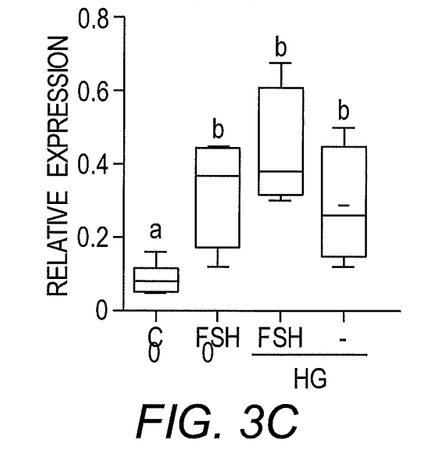
FIG. 3C, FIG. 3D and FIG. 3E respectively show IGF2, StAR, and Cyp11a1 relative mRNA expression in primary human granulosa cells after treatment with vehicle, FSH, FSH+HG, or HG alone for 48 hours.

Example 3: Pharmacological Inhibition of SIK Activity Enhances FSH Actions in Humans The effect of SIK inhibition in primary human granulosa cells was subsequently demonstrated. As in rodents, SIK inhibition in human granulosa cells potentiated FSH stimulation of CYP19a1 mRNA expression (FIG. 3A) and Cyp19a1 promoter activation (FIG. 3B). The impact of SIK on the expression of insulin-like growth factor 2, which is expressed exclusively in human granulosa cells and strongly stimulated by FSH (Baumgarten, et al. (2015) *J. Clin. Endocrinol. Metab.* 100(8):E1046-105) was also examined. The addition of SIK inhibitors to the media enhanced the stimulatory effect of FSH on IGF2 mRNA expression (FIG. 3C). Although IGF2 levels tended to be higher in cells treated with FSH and HG-9-91-01 when compared to cells treated with FSH alone, the difference was not statistically significant. Interestingly, SIK inhibition by HG-9-91-01 in the absence of FSH increased IGF2 mRNA levels significantly when compared to controls (FIG. 3C).

Figure 3D:
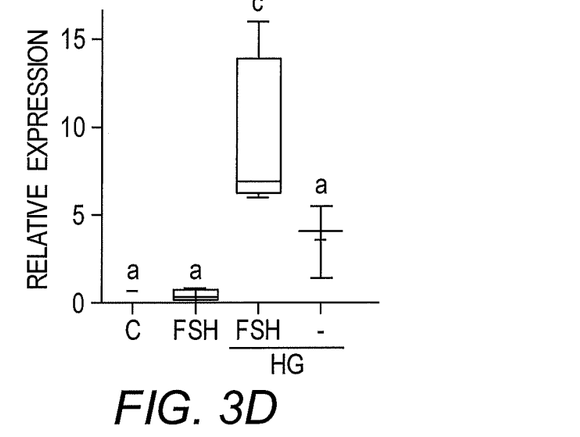
Figure 3E:
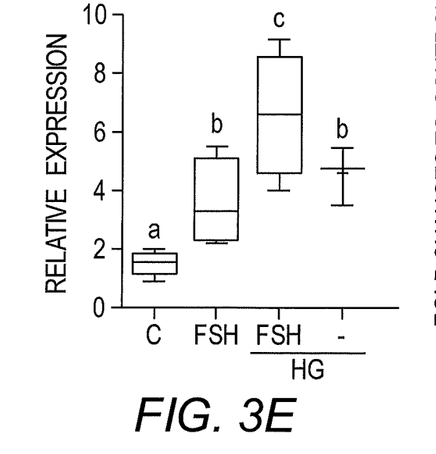
Figure 3F:
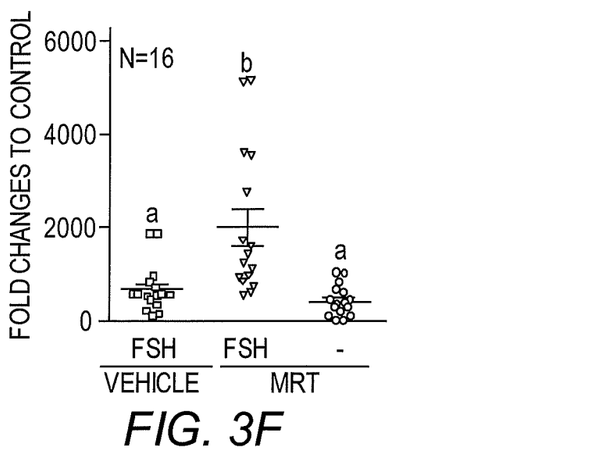
FIG. 3F shows aromatase expression in primary human granulosa cells after treatment with FSH, FSH+MRT67307 (MRT), or MRT alone. Different letters represent significant differences (mean±SEM, N≥7, one-way ANOVA followed by Tukey, $p<0.05$).

SIK inhibition also potentiated the stimulatory effect of FSH on steroidogenic acute regulator (STARD1, a.k.a. StAR) and cholesterol side-chain cleavage (CYP11a1, a.k.a. P450scc) mRNA levels (FIG. 3D and FIG. 3E), which are known to increase after treatment of human granulosa cells with FSH (Baumgarten, et al. (2015) *J. Clin. Endocrinol. Metab.* 100(8):E1046-105; Baumgarten, et al. (2014) *J. Clin. Endocrinol. Metab.* 99(8):2995-3004). Moreover, as observed for CYP19a1, treatment with HG-9-91-01 alone was enough to increase STARD1 and CYP11A1 mRNA levels. To further support this conclusion, a second inhibitor and a larger cohort of patients (n=16) were used to study the effect of SIK activity on CYP19A1 mRNA levels. In this larger experiment, the combination of FSH plus MRT67307 significantly increased CYP19A1 mRNA levels by 3-fold when compared to cells treated with FSH only (P<0.0001) (FIG. 3F). In contrast to HG-9-91-01, treatment with MRT67307 alone did not affect CYP19A1 mRNA levels.

Example 4: SIK Isoform Expression in the Ovary and Granulosa Cells

Figure 4:
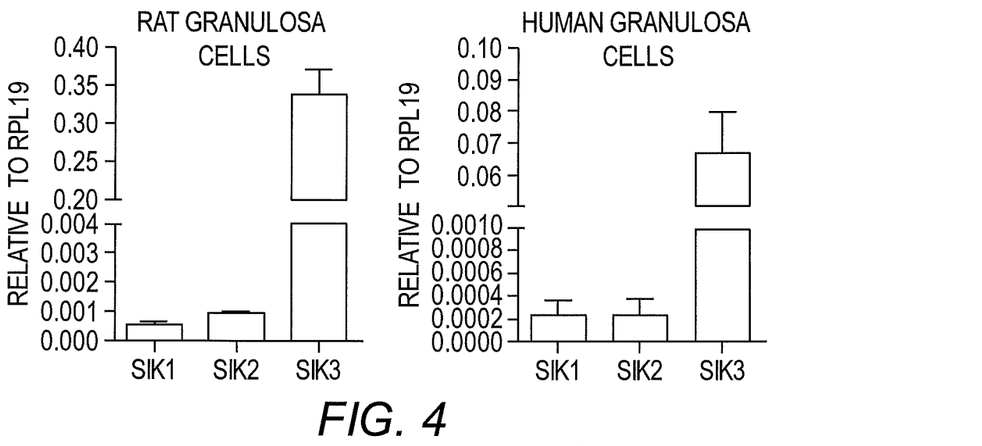
FIG. 4 shows relative SIK1, SIK2, and SIK3 mRNA expression levels in rat and human granulosa cells. Bars represent mean±SEM.

Since the expression of SIKs in the ovary has not been previously investigated, the mRNA levels of SIK isoforms in rat and human granulosa cells was quantified. The mRNA for all isoforms was detected in the granulosa cells of both species, although the relative expression of Sik1 and Sik2 mRNAs was lower than the expression of Sik3 (FIG. 4). While western blot analysis confirmed the expression of each isoform in rat granulosa cells, Sik1 and Sik2 were more easily detected than Sik3.

As observed at the mRNA level in rat granulosa cells, immunohistochemical studies of rat ovaries showed a robust signal for SIK2 and SIK3 proteins while the SIK1 protein signal was substantially lower. These studies also showed that granulosa cells express both SIK2 and SIK3, while the interstitial tissue and the theca cells express mostly SIK3. The expression of SIKs in rat granulosa cells was further visualized using immunofluorescence, which showed a strong signal for SIK2 and SIK3, while the SIK1 signal was significantly lower and almost undetectable.

Example 5: Knockdown of SIK2 Enhances FSH Actions

Figure 5A:
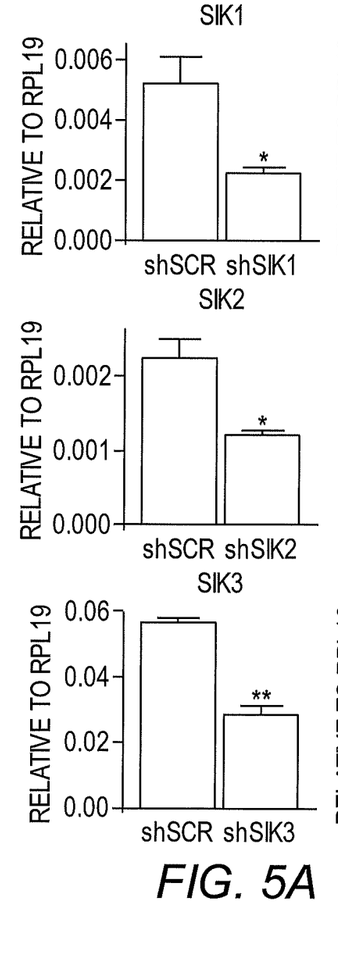

Small interference RNAs were used to selectively knock-down SIK1, SIK2, or SIK3 and gain insight into the role of individual SIK isoforms. Rat granulosa cells were infected with lentivirus carrying small hairpin (sh) RNA specific for each isoform according to established methods (Wu, et al. (2013) *Mol. Cell Biol.* 33(15):2817-2828). FSH or vehicle was added to the media 48 hours after virus infection. Subsequently, the cells were incubated for an additional 48 hours. Each SIK shRNA significantly knocked down its respective SIK isoform when compared to cells infected with a control shRNA (FIG. 5A).

Figure 5B:
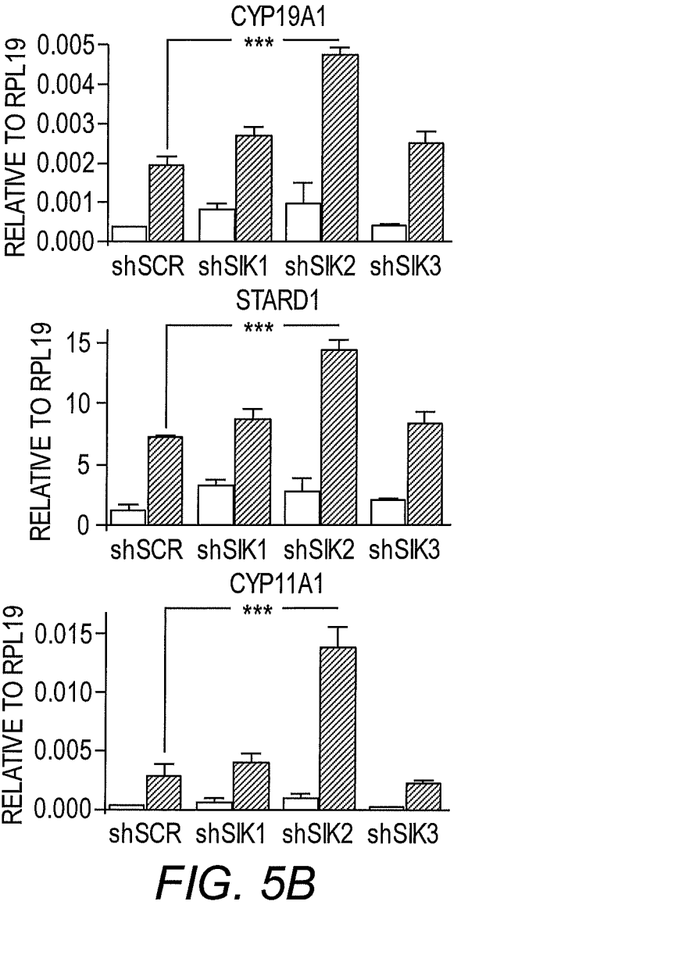
FIG. 5B, Cyp19a1, STARD1, and CYP11a1 relative mRNA expression levels after exposure to shSCR, shSIK1, shSIK2, or shSIK3. Cells were treated with vehicle (white bars) or FSH (filled bars). *$p<0.001$, t-test, n=3.

In addition to aromatase (CYP19a1), the effect of SIK knockdown on the expression of additional targets of FSH were examined, including STARD1 and CYP11a1. The knockdown of SIK1 or SIK3 did not enhance CYP19a1, STARD1, or CYP11A1 mRNA expression in the presence or absence of FSH. In contrast, SIK2 knockdown potentiated the stimulatory effect of FSH on the three genes (FIG. 5B), indicating a leading role of SIK2 in the regulation of the response of granulosa cells to FSH.

Figure 5C:
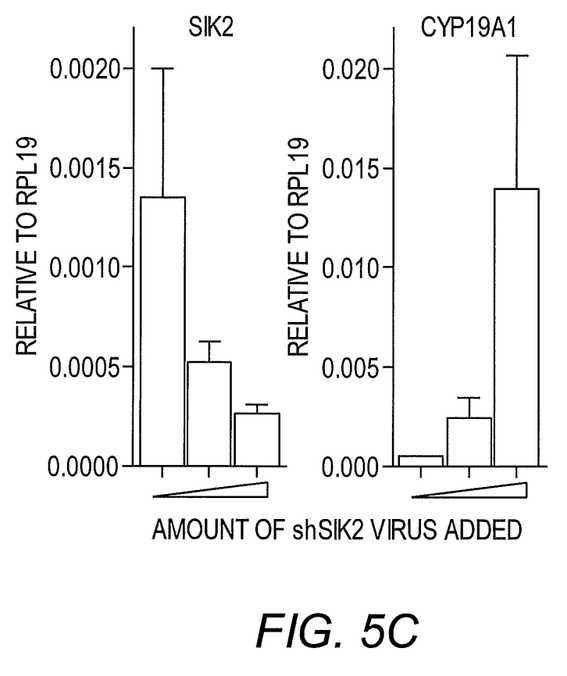
FIG. 5C, Inverse correlation between SIK2 knockdown with CYP19a1 expression in rat granulosa cells. Cells were exposed to increasing concentrations of shSIK2 for 48 hours and then treated with FSH for an additional 48 hours (n=3).
Figure 5D:
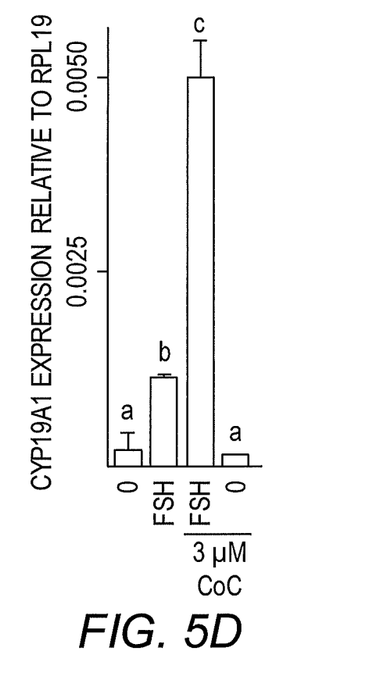
FIG. 5D, Compound C (CoC), a SIK2 inhibitor, potentiates FSH action but alone has no effect. Different letters differ significantly, ANOVA (n=3).

To further confirm the role of SIK2 on CYP19a1 expression, granulosa cells were infected with increasing amounts of anti-SIK2 shRNA (shSIK2) and cultured in the presence of FSH for 48 hours. An increase in CYP19A1 mRNA levels proportional and concomitant with a decrease in SIK2 mRNA levels was observed (FIG. 5C). Moreover, granulosa cells treated with Compound C, which has been previously shown to prevent SIK2-mediated suppression of a cAMP reporter without suppressing SIK1 and SIK3 activity (Sasaki, et al. (2011) *Neuron* 69(1):106-119), showed that Compound C strongly potentiated the stimulatory effect of FSH on CYP19A1 (FIG. 5D). However, in contrast to HG-9-91-01, Compound C alone failed to upregulate CYP19A1 mRNA levels.

Example 6: Effect of SIK Inhibition in IVF Patients with Different Etiologies

The effect of SIK inhibition on CYP19A1 protein expression in the granulosa cells of patients with normal (tubal, malefactors, endometriosis) or abnormal (polycystic ovarian syndrome (PCOS), anovulation) ovarian function was examined. In patients with normal ovarian function, FSH strongly increased CYP19A1 protein levels, an effect that was potentiated by the inhibition of SIK activity. In the absence of FSH, SIK inhibition stimulated CYP19A1 protein expression in three of the four patients with normal ovarian function.

Figure 6:
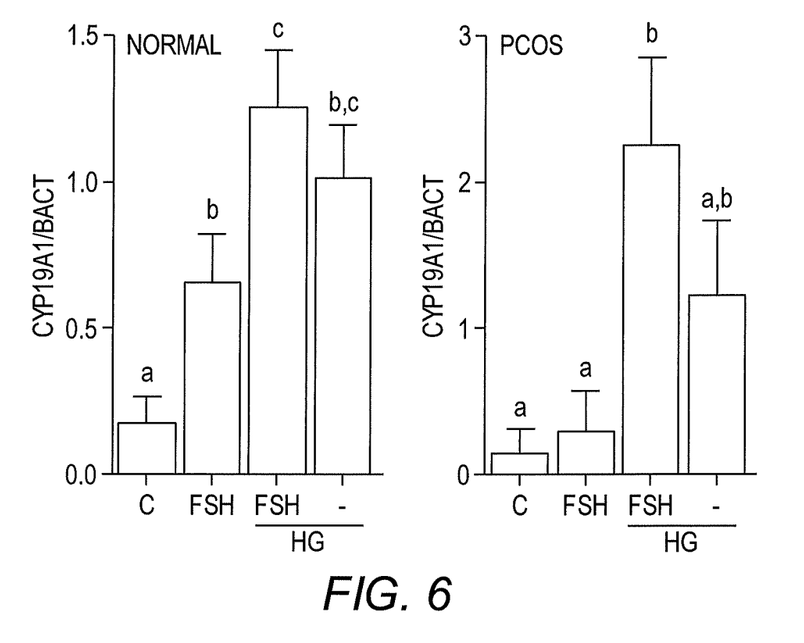
FIG. 6 shows SIK inhibition rescues FSH actions in human granulosa cells from patients with different etiologies of infertility. Primary granulosa cells were obtained from patients with normal ovarian function (left panel) or patients diagnosed with polycystic ovarian syndrome or anovulation (right panel). Cells were treated with vehicle, FSH, FSH plus HG-9-91-01 (HG), or HG alone for 48 hours. CYP19a1 and β-actin (BACT) protein levels were measured 48 hours after the initiation of treatment by western blot. The intensity of the CYP19a1 and BACT bands was quantified, and the data expressed as a ratio between aromatase and BACT. Different letters represent significant differences, one-way ANOVA followed by Tukey test, $p<0.05$, (n=5).

In contrast, FSH was unable to stimulate CYP19A1 in two of the three patients with PCOS, while SIK inhibition rescued FSH induction of CYP19A1 in these two patients (FIG. 6). In the PCOS patient that responded to FSH alone, the presence of a SIK inhibitor potentiated FSH actions. In the patient with anovulation, FSH stimulated CYP19A1 mRNA levels marginally, while HG alone or in the presence of FSH stimulated CYP19A1 strongly (FIG. 6).

Figure 7:
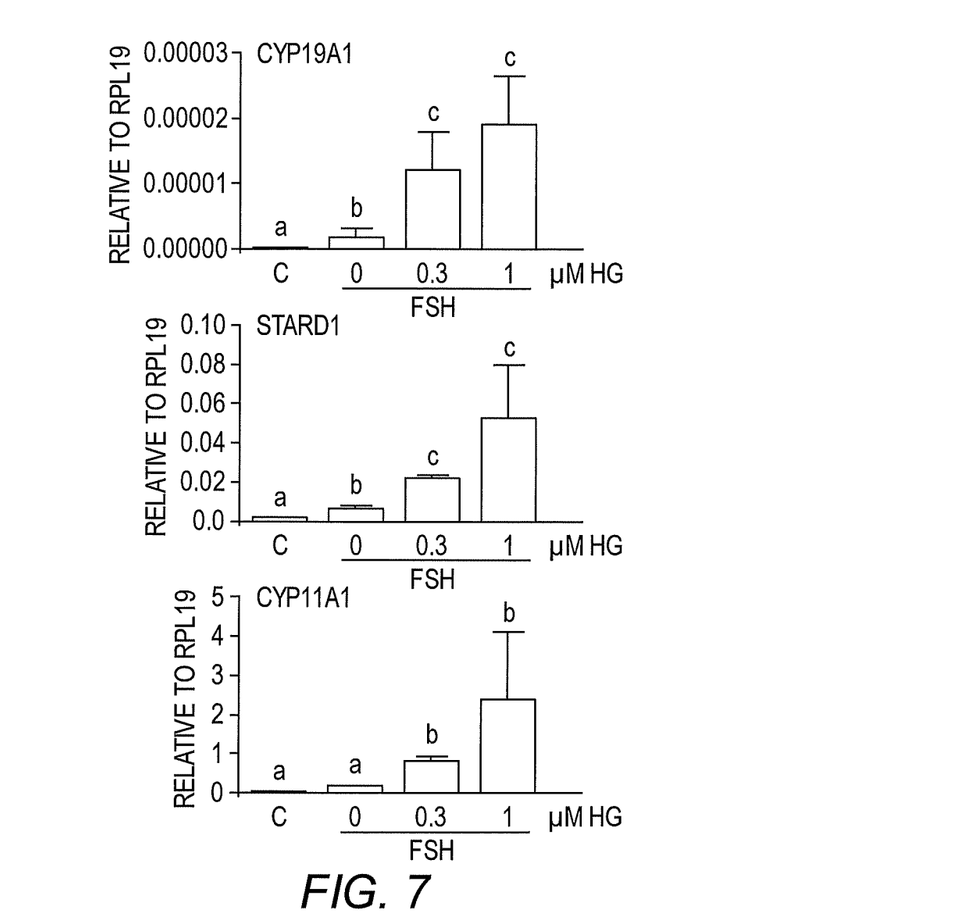
FIG. 7 shows the effect of SIK inhibition in mouse granulosa cells. Primary mouse granulosa cells were treated with vehicle, FSH, or FSH plus increasing concentrations of HG-9-91-01 (HG). Cyp19a1, StAR, and P450scc mRNA levels were quantified 48 hours later and expressed as relative levels to Rp119. Different letters represent significant differences (mean±SEM, n=5, one-way ANOVA followed by Tukey, $p<0.05$).

Example 7: Effect of SIK Inhibition in Mouse Granulosa Cells In Vitro and In Vivo To demonstrate the role of SIK in ovarian function using genetic models, the in vivo effect of SIK inhibition on the function of granulosa cells isolated from wild-type mice was examined. The results of these experiments mirrored those in rat and human granulosa cells. Thus, as shown in FIG. 7, inhibition of SIK activity potentiated the stimulation of Cyp19a1, Stard1, and Cyp19a11 mRNA levels by FSH.

Figure 8A:
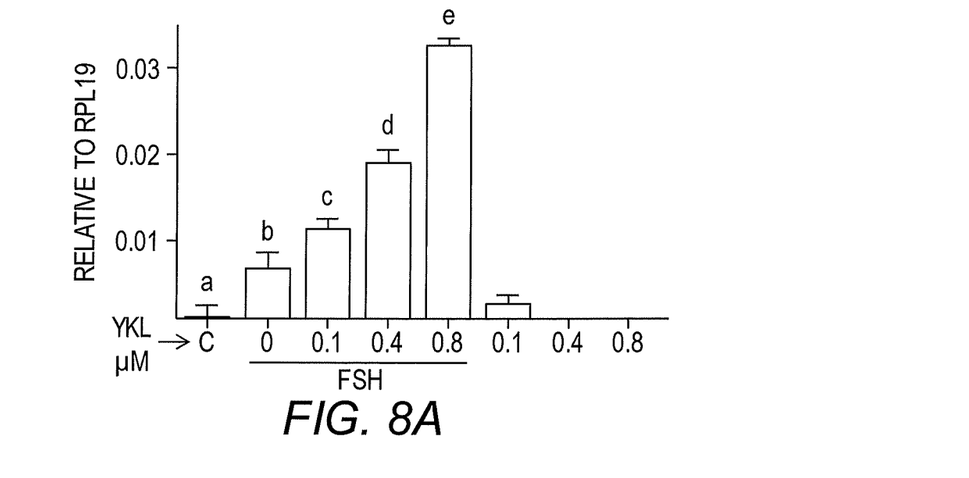

As mouse granulosa cells responded similarly to rat and human cells, the effect of SIK activity inhibition in vivo was examined. For this purpose, it was required to test a SIK inhibitor suitable for in vivo studies since the inhibitors used above have a short half-life in vivo. Thus, the effect of YKL-05-099 was examined. This inhibitor has been shown to achieve free $IC_{50}$ serum concentrations for SIK inhibition for more than 16 hours (Sundberg, et al. (2016) *ACS Chem. Biol.* 11(8):2105-2111). In vivo, YKL-05-099 reduces phosphorylation of a known SIK substrate and is more tolerable and soluble than other SIK inhibitors (Sundberg, et al. (2016) *ACS Chem. Biol.* 11(8):2105-2111). Confirmatory in vitro experiments demonstrated that YKL-05-099 also enhances the stimulatory effect of FSH on Cyp19a1 mRNA expression in a concentration-dependent manner (FIG. 8A).

Figure 8B:
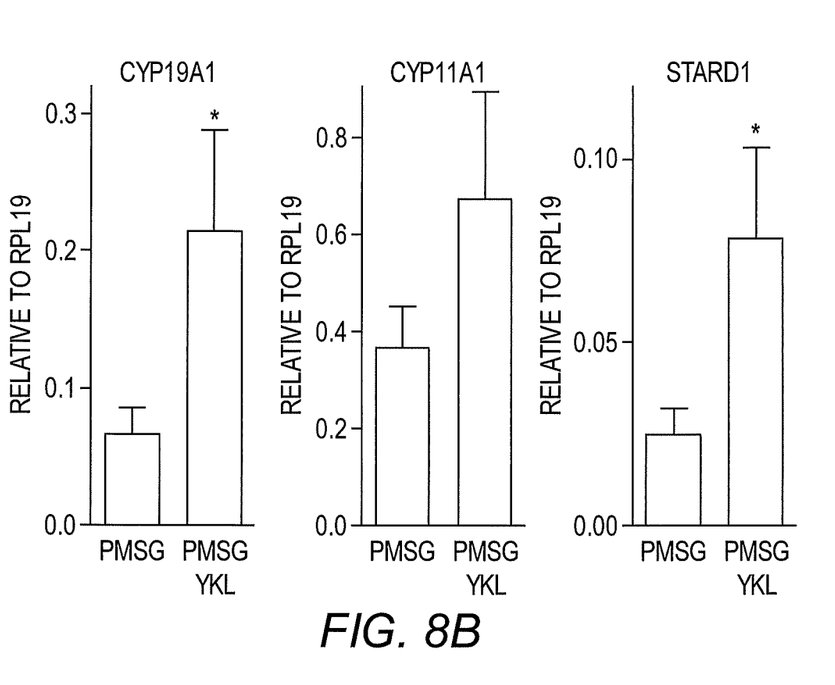
FIG. 8B, Immature 23-day-old female mice were injected i.p. with YKL or vehicle (PBS). Two hours later, animals were treated with PMSG or PMSG plus YKL. The expression of CYP19a1, CYP11a1, and STARD1 was quantified 48 hours later. *$p<0.05$, t-test, n=7.

Immature, 23-day-old female mice were injected with vehicle or YKL-05-099 before the administration of PMSG, an analog of FSH. The mRNA levels for Cyp19a1, Cyp11a1, and Stard1 were high in the granulosa cells of animals treated with PMSG. Pretreatment with YKL-05-099 enhanced the stimulatory effect of PMSG on Cyp19a1 and Stard1 significantly; whereas, only a trend to increase Cyp11a1 mRNA induction was observed (FIG. 8B).

What is claimed is:

1. A method for improving, restoring or enhancing fertility in a female subject comprising administering to the female subject an effective amount of an inhibitor of salt-inducible kinase 2 (SIK2) in combination with an agent of an ovulation induction regimen thereby improving, restoring or enhancing fertility in the female subject, wherein the inhibitor is HG-9-91-01, MRT67307, MRT199665, Dorsomorphin, YKL-06-061, KIN-112, ARN3236, ARN3261, Dasatinib, Bosutinib, or TAE-684.

2. The method of claim 1, wherein release of oocytes in the female subject is increased.

3. The method of claim 1, wherein the agent of the ovulation induction regimen is a gonadotropin-releasing hormone agonist, human menopausal gonadotropin, follicle-stimulating hormone, clomiphene citrate or human chorionic gonadotropin.

4. The method of claim 1, wherein the female subject has a diminished ovarian response to gonadotropins.

5. The method of claim 1, wherein the female subject is older than 35 years of age.

6. A method for increasing oocyte production in a female subject comprising administering to the female subject an effective amount of an inhibitor of salt-inducible kinase 2 (SIK2) in combination with an agent of an ovulation induction regimen thereby increasing oocyte production in the female subject, wherein the inhibitor is HG-9-91-01, MRT67307, MRT199665, Dorsomorphin, YKL-06-061, KIN-112, ARN3236, ARN3261, Dasatinib, Bosutinib, or TAE-684.

7. The method of claim 6, wherein the agent of the ovulation induction regimen is a gonadotropin-releasing hormone agonist, human menopausal gonadotropin, follicle-stimulating hormone, clomiphene citrate or human chorionic gonadotropin.

8. The method of claim 6, wherein the female subject has a diminished ovarian response to gonadotropins.

9. The method of claim 6, wherein the female subject is older than 35 years of age.

10. A method for improving, restoring or enhancing fertility in a female subject comprising administering to the female subject an effective amount of YKL-05-099 in combination with follicle-stimulating hormone thereby improving, restoring or enhancing fertility in the female subject.

11. The method of claim 10, wherein release of oocytes in the female subject is increased.

12. The method of claim 10, wherein the female subject has a diminished ovarian response to gonadotropins.

13. The method of claim 10, wherein the female subject is older than 35 years of age.

14. A method for increasing oocyte production in a female subject comprising administering to the female subject an effective amount of YKL-05-099 in combination with follicle-stimulating hormone thereby increasing oocyte production in the female subject.

15. The method of claim 14, wherein the female subject has a diminished ovarian response to gonadotropins.

16. The method of claim 14, wherein the female subject is older than 35 years of age.

17. A method for improving, restoring or enhancing fertility in a female subject comprising administering to the female subject an effective amount of an inhibitor of salt-inducible kinase 2 (SIK2) in combination with follicle-stimulating hormone thereby improving, restoring or enhancing fertility in the female subject, wherein the inhibitor is HG-9-91-01, MRT67307, MRT199665, Dorsomorphin, YKL-06-061, KIN-112, ARN3236, ARN3261, Dasatinib, Bosutinib, or TAE-684.

18. The method of claim 17, wherein release of oocytes in the female subject is increased.

19. The method of claim 17, wherein the female subject has a diminished ovarian response to gonadotropins.

20. The method of claim 17, wherein the female subject is older than 35 years of age.

21. A method for increasing oocyte production in a female subject comprising administering to the female subject an effective amount of an inhibitor of salt-inducible kinase 2 (SIK2) in combination with follicle-stimulating hormone thereby increasing oocyte production in the female subject, wherein the inhibitor is HG-9-91-01, MRT67307, MRT199665, Dorsomorphin, YKL-06-061, KIN-112, ARN3236, ARN3261, Dasatinib, Bosutinib, or TAE-684.

22. The method of claim 21, wherein the female subject has a diminished ovarian response to gonadotropins.

23. The method of claim 21, wherein the female subject is older than 35 years of age.

24. A method for improving, restoring or enhancing fertility in a female subject comprising administering to the female subject an effective amount of YKL-05-099 in combination with an agent of an ovulation induction regimen thereby improving, restoring or enhancing fertility in the female subject.

25. The method of claim 24, wherein release of oocytes in the female subject is increased.

26. The method of claim 24, wherein female subject has a diminished ovarian response to gonadotropins.

27. The method of claim 24, wherein the female subject is older than 35 years of age.

28. The method of claim 24, wherein the agent of the ovulation induction regimen is a gonadotropin-releasing hormone agonist, human menopausal gonadotropin, follicle-stimulating hormone, clomiphene citrate or human chorionic gonadotropin.

29. A method for increasing oocyte production in a female subject comprising administering to the female subject an effective amount of YKL-05-099 in combination with an agent of an ovulation induction regimen thereby increasing oocyte production in the female subject.

30. The method of claim 29, wherein the female subject has a diminished ovarian response to gonadotropins.

31. The method of claim 29, wherein the female subject is older than 35 years of age.

32. The method of claim 29, wherein the agent of the ovulation induction regimen is a gonadotropin-releasing hormone agonist, human menopausal gonadotropin, follicle-stimulating hormone, clomiphene citrate or human chorionic gonadotropin.

* * * * *